(12) United States Patent
Govea (10) Patent No.: US 9,302,094 B2
(45) Date of Patent: Apr. 5, 2016

(54) LEAD ANCHOR WITH PIVOTABLE PADDLES AND SYSTEMS AND METHODS USING THE LEAD ANCHOR

(71) Applicant: BOSTON SCIENTIFIC NEUROMODULATION CORPORATION, Valencia, CA (US)

(72) Inventor: Michael X. Govea, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/519,490

(22) Filed: Oct. 21, 2014

(65) Prior Publication Data
US 2015/0119965 A1   Apr. 30, 2015

Related U.S. Application Data

(60) Provisional application No. 61/895,818, filed on Oct. 25, 2013.

(51) Int. Cl.
| A61N 1/05 | (2006.01) |
| A61N 1/375 | (2006.01) |
| A61N 1/36 | (2006.01) |
| A61N 1/362 | (2006.01) |

(52) U.S. Cl.
CPC .............. *A61N 1/0539* (2013.01); *A61N 1/059* (2013.01); *A61N 1/0553* (2013.01); *A61N 1/0558* (2013.01); *A61N 1/375* (2013.01); *A61N 1/362* (2013.01); *A61N 1/3605* (2013.01); *A61N 1/3752* (2013.01)

(58) Field of Classification Search
CPC .... A61N 1/0553; A61N 1/0558; A61N 1/059; A61N 1/375; A61N 1/3605; A61N 1/362; A61N 1/3752
USPC .......................................... 607/116–117, 136
See application file for complete search history.

(56) References Cited

U.S. PATENT DOCUMENTS

| 6,181,969 | B1 | 1/2001 | Gord |
| 6,516,227 | B1 | 2/2003 | Meadows et al. |
| 6,609,029 | B1 | 8/2003 | Mann et al. |
| 6,609,032 | B1 | 8/2003 | Woods et al. |
| 6,741,892 | B1 | 5/2004 | Meadows et al. |
| 7,244,150 | B1 | 7/2007 | Brase et al. |
| 7,437,193 | B2 | 10/2008 | Parramon et al. |
| 7,672,734 | B2 | 3/2010 | Anderson et al. |
| 7,761,165 | B1 | 7/2010 | He et al. |
| 7,949,395 | B2 | 5/2011 | Kuzma |
| 7,974,706 | B2 | 7/2011 | Moffitt et al. |
| 8,140,172 | B1 | 3/2012 | Jones et al. |
| 8,175,710 | B2 | 5/2012 | He |
| 8,224,450 | B2 | 7/2012 | Brase |
| 8,364,278 | B2 | 1/2013 | Pianca et al. |
| 8,892,216 | B2 | 11/2014 | Leven |
| 2007/0150036 | A1 | 6/2007 | Anderson |

*Primary Examiner* — Paula J Stice
(74) *Attorney, Agent, or Firm* — Lowe Graham Jones PLLC; Bruce E. Black (57) ABSTRACT

A lead anchor includes a first paddle assembly and a flexible housing. The first paddle assembly includes an assembly housing, an actuator, and at least one pivotable paddle attached to the housing and operably coupled to the actuator. The at least one pivotable paddle is suitably arranged to pivot out of the assembly housing when a user operates the actuator. The lead anchor also includes a flexible housing disposed around the first paddle assembly and defining at least one lead lumen extending adjacent to the first paddle assembly so that the at least one pivotable paddle pivots into a one of the at least one lead lumen to constrain any lead disposed within the one of the at least one lead lumen.

10 Claims, 8 Drawing Sheets

LEAD ANCHOR WITH PIVOTABLE PADDLES AND SYSTEMS AND METHODS USING THE LEAD ANCHOR

CROSS-REFERENCE TO RELATED APPLICATIONS

This application claims the benefit under 35 U.S.C. §119 (e) of U.S. Provisional Patent Application Ser. No. 61/895,818, filed Oct. 25, 2013, which is incorporated herein by reference.

FIELD

The present invention is directed to the area of implantable electrical stimulation systems and methods of making and using the systems. The present invention is also directed to implantable lead anchors and electrical stimulation systems incorporating the lead anchors, as well as methods of making and using the lead anchors and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Often leads are anchored at one or more places within the body to prevent or reduce the movement of the lead or stimulator electrodes after implantation. Such undesired movement of the leads may lead to: (1) damage to surrounding tissue; (2) movement of the stimulator electrodes out of their desired positions in such a way as to reduce effectiveness of treatment; or (3) interference or interruption in the connections between the stimulator electrodes and the control module.

BRIEF SUMMARY

One embodiment is a lead anchor having a first paddle assembly including an assembly housing, an actuator, and at least one pivotable paddle attached to the housing and operably coupled to the actuator. The at least one pivotable paddle is suitably arranged to pivot out of the assembly housing when a user operates the actuator. The lead anchor also includes a flexible housing disposed around the first paddle assembly and defining at least one lead lumen extending adjacent to the first paddle assembly so that the at least one pivotable paddle pivots into a one of the at least one lead lumen to constrain any lead disposed within the one of the at least one lead lumen.

Another embodiment is a lead anchor including a first paddle assembly having an assembly housing, an actuator, and two pivotable paddles attached to the housing and operably coupled to the actuator. The two pivotable paddles are suitably arranged to pivot out of opposite sides of the assembly housing when a user operates the actuator. The lead anchor also includes a flexible housing disposed around the first paddle assembly and defining two lead lumens extending adjacent to the opposite sides of the first paddle assembly so that the two pivotable paddles each pivot into a respective one of the two lead lumens.

Yet another embodiment is a kit including a first implantable stimulation lead and either of the lead anchors described above. The lead anchor is suitably arranged to receive a portion of the first implantable stimulation lead within a lead lumen of the lead anchor.

A further embodiment is a method of using any of the lead anchors described above. The method may include inserting a portion of a first electrical stimulation lead into a lead lumen of the lead anchor. The method may also include actuating the actuator of the first paddle assembly to pivot the paddle(s) so that at least one of the paddle(s) engages the first electrical stimulation lead and constrains the first electrical stimulation lead within the lead lumen.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed implantable lead anchors and electrical stimulation systems incorporating the lead anchors, as well as methods of making and using the lead anchors and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
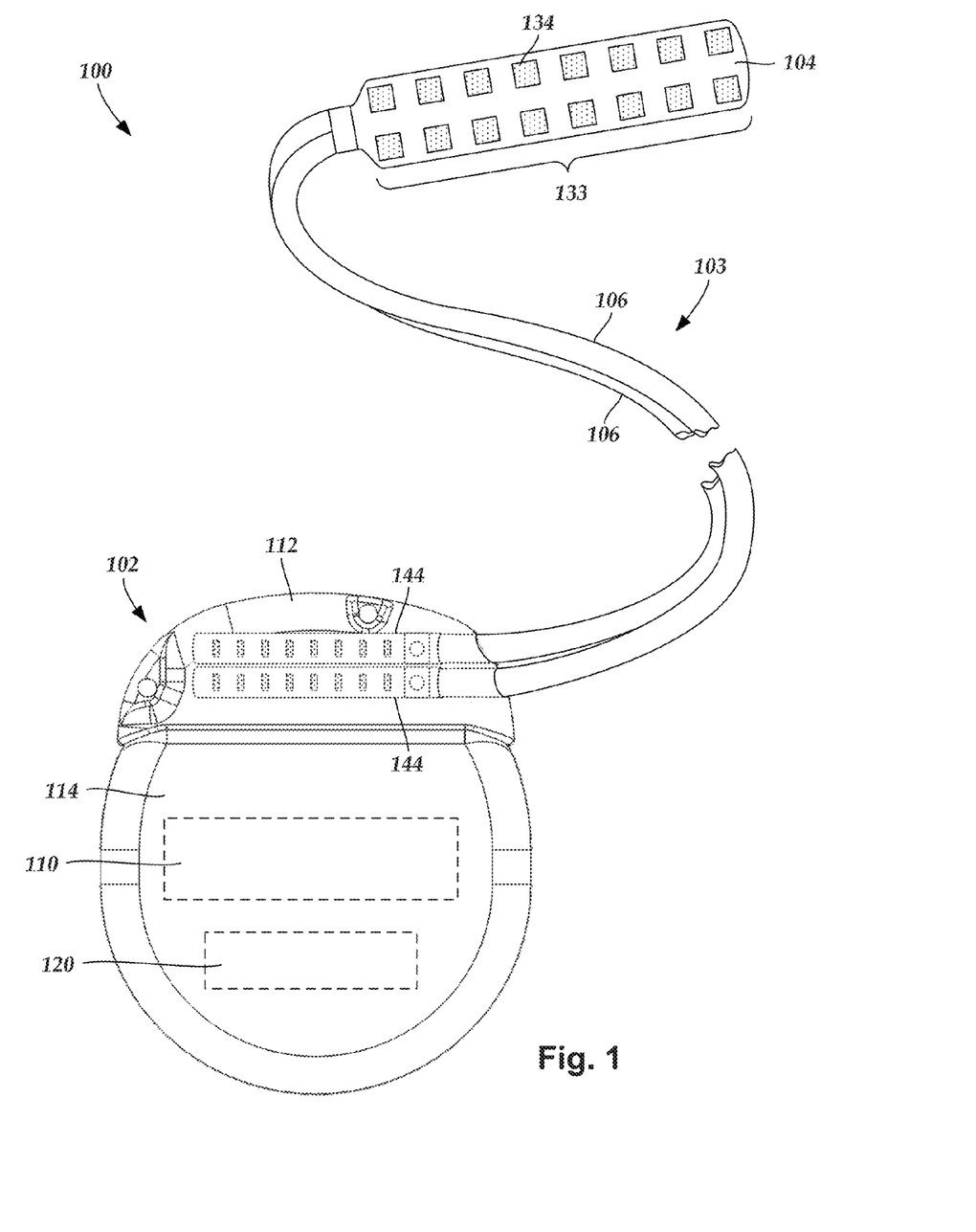
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system 100 includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array 133 of electrodes, such as electrode 134, is disposed on the paddle body 104, and an array of terminals (e.g., 310 in FIG. 3A-3B) is disposed along each of the one or more lead bodies 106.

It will be understood that the electrical stimulation system 100 can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
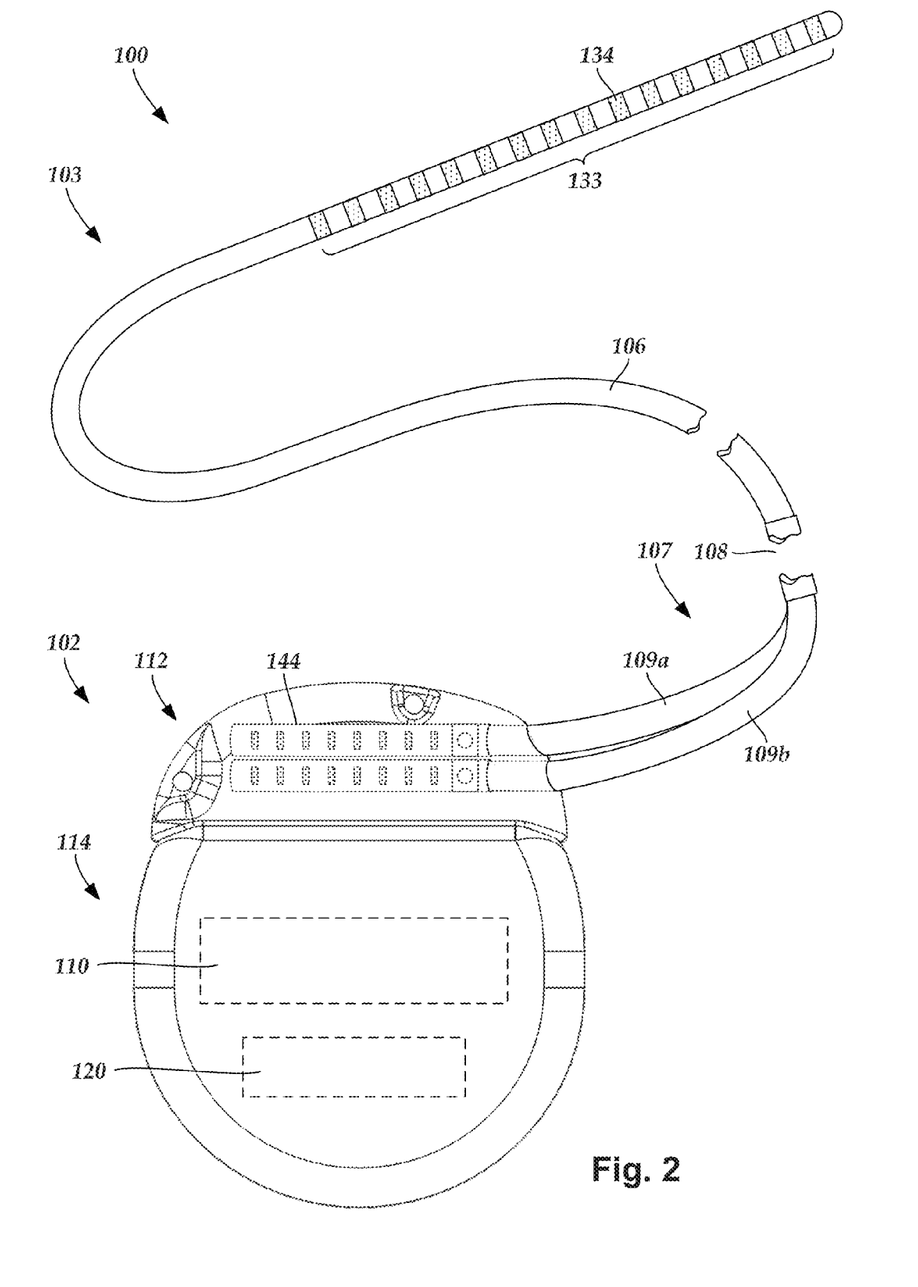
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (324 in FIG. 3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 207 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

With reference to FIGS. 1 and 2, the control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
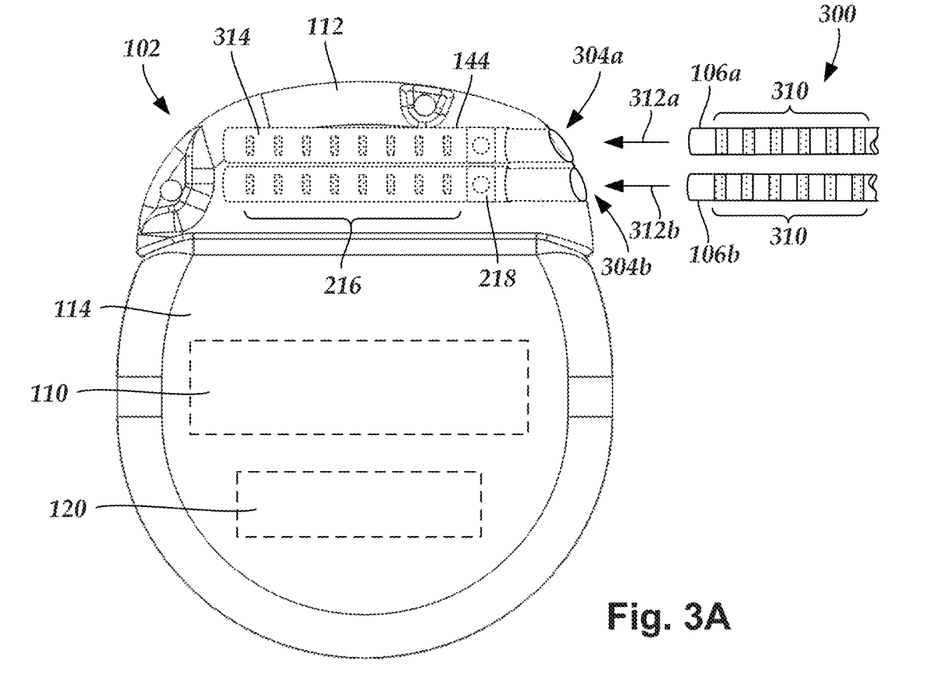
FIG. 3A is a schematic view of one embodiment of the control module of FIG. 1 configured and arranged to electrically couple to an elongated device, according to the invention.
Figure 3B:
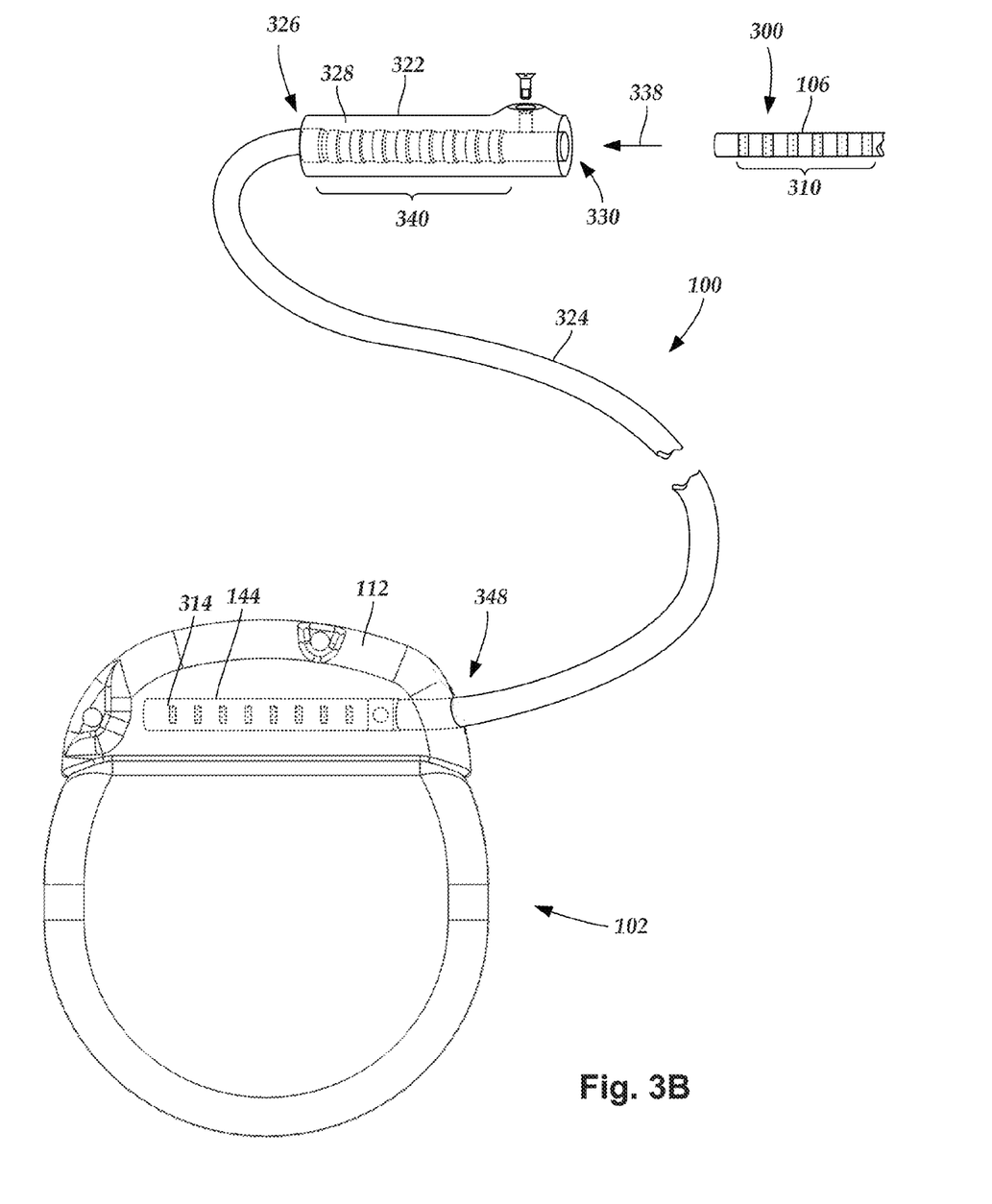
FIG. 3B is a schematic view of one embodiment of a lead extension configured and arranged to electrically couple the elongated device of FIG. 2 to the control module of FIG. 1, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIGS. 3A and 3B). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 207 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contacts 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

Figure 4A:
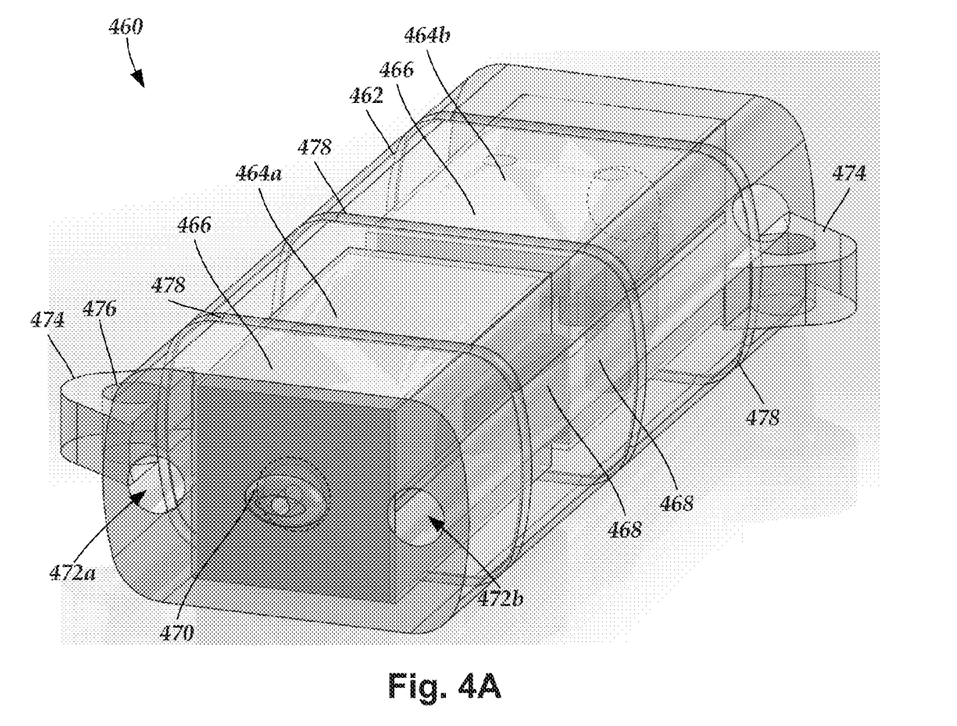
FIG. 4A is a schematic perspective view of one embodiment of a lead anchor, according to the invention.

Turning to FIG. 4A, a lead anchor 460 is shown for anchoring leads (such as the lead 103 of FIG. 2) and/or lead extensions (such as the lead extension 324 of FIG. 3B) to a patient's tissue. The lead anchor 460 includes an outer housing 462 having one or more lead lumens, for example, a first lead lumen 472a and a second lead lumen 472b. The lead lumens 472a, 472b are located adjacent to one or more paddle assemblies, for example, a first paddle assembly 464a and a second paddle assembly 464b. Either one or both of the paddle assemblies 464a, 464b may be included in the lead anchor 460. The outer housing 462 may be formed from any suitable biocompatible material that is flexible for operation of the lead anchor with respect to the paddles described below and is preferably non-rigid, or avoids sharp corners, to reduce or prevent damage to the surrounding tissue. Examples of such material include a plastic or polymer, such as, silicone, polyvinylchloride, polyurethane, or the like, or any combination of these materials.

The lead lumens 472a, 472b extend longitudinally through the outer housing 462 along the length of the anchor 460. Leads (such as lead 103 of FIG. 2) and/or lead extensions (such as lead extension 324 in FIG. 3B) may be inserted into the lead lumens 472a, 472b from either a first end or an opposing second end of the lead anchor 460 through lumen openings at the respective end. In at least some embodiments, the lead lumens 472a, 472b have diameters equal to or slightly larger or smaller than the diameters of portions of the leads or lead extensions to be received in the lead lumens 472a, 472b.

Figure 4B:
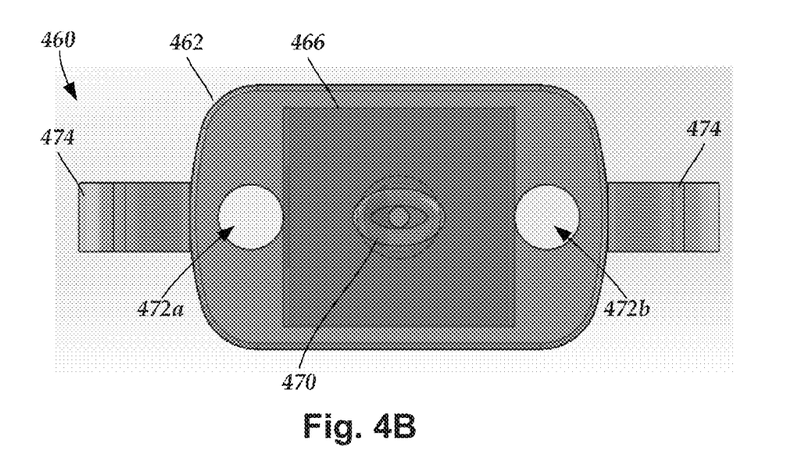
FIG. 4B is a schematic front view of the lead anchor of FIG. 4A, according to the invention.

In FIGS. 4A-4B, the lead lumens 472a, 472b are shown with circular cross-sectional shapes. However, other cross-sectional shapes are also possible including, for example, triangular, rectangular, ovoid, or the like. The lead lumens 472a, 472b may be formed by any suitable method, such as molding, piercing, boring, reaming, tapping, or the like. In some embodiments, the lead lumens 472a, 472b include one or more threads, ridges, micro patterns, or other structural features partially or completely along their length to facilitate or enhance engagement with the lead 103 or lead extension 324.

Each paddle assembly 464a, 464b includes an assembly housing 466, one or more pivoting paddles 468, and an actuator 470. Each of the paddles 468, the actuator 470, and the assembly housing 466 may be made of the same or different suitable biocompatible materials, which are sufficiently rigid to perform their functions within the lead anchor 460. Examples of these materials include metals, polymers, metal-polymer composites, or the like.

The assembly housing 466 includes one or more slots. In the illustrated embodiment, the slots are on opposite transverse sides. These slots may extend substantially along the longitudinal length of the assembly housing 466. The paddles 468 pivot out of the slots into the lead lumens 472a, 472b to engage a lead or lead extension in the respective lead lumen and hold the lead or lead extension in the lead lumen.

In at least some embodiments, the paddles 468 are located adjacent to the actuator 470 and the longitudinal slots in a horizontal plane. In at least some embodiments, the paddles 468 are substantially aligned along the longitudinal axis of the outer housing 462 so that the paddles 468 are clear of the lead lumens 472a, 472b in a closed position. In at least some embodiments, the paddles 468 are arranged to pivot about a vertical axis perpendicular to the longitudinal axis of the assembly housing 466 and extend transversely outwards from opposite sides of the assembly housing 466. The pivoting paddles 468 extend out through the longitudinal slots to secure lead portions in the lead lumens 472a, 472b. Such extension of the paddles 468 may be based on actuation of the actuator 470. It will be understood that the one or more paddles 468 may be arranged in different orientations within the assembly housing 466 suitable for pivoting into the lead lumens 472a, 472b.

The actuator 470 is a device configured to pivot the paddles 468 out of the paddle assemblies and into the lead lumens 472a, 472b. For example, the actuator 470 may extend towards the paddles 468 along the longitudinal axis of the assembly housing 466 to engage with the paddles 468. The actuator 470 may be a screw or any other suitable mechanical or electromechanical device or arrangement. The actuator 470 may include ridges or any other suitable structure on its outer surface to frictionally hold the actuator 470 at a particular position within the paddle assembly 464a, 464b, and therefore control the movement of the actuator 470.

The lead anchor 460 is anchored to a patient's tissue in any suitable manner. In FIGS. 4A and 4B, one or more suture tabs 474 are shown attached to the outer surface of the outer housing 462. The suture tabs 474 include one or more suture holes 476 to receive sutures, staples, or the like for anchoring the lead anchor 460 to the patient's tissue. In some embodiments, the suture tabs 474 are made of the same material as the material of the outer housing 462. In some embodiments, the suture tabs 474 and the outer housing 462 are unitary. The suture tabs 474 may be formed using any suitable method such as, molding, piercing, boring, reaming, tapping, or the like.

In at least some embodiments, one or more suture grooves 478 are defined along the outer surface of the outer housing 462. In FIGS. 4A-4B, the suture grooves 478 are shown as depressions on the outer surface of the housing 462 and extend circumferentially about at least a portion of a circumference of the outer housing 462. In at least some embodiments, at least one of the suture grooves 478 is aligned longitudinally with at least one of the suture holes 476 along the outer housing 462. The suture grooves 478 may facilitate extending sutures around at least a portion of a cross-sectional circumference of the outer housing 462 during lead implantation, while preventing the sutures from sliding off an end of the lead anchor 460 during subsequent patient movement.

Referring to FIG. 4B, a schematic front view of the lead anchor 460 of FIG. 4A is shown. As discussed above, the lead anchor 460 includes the lead lumens 472a, 472b located adjacent to the paddle assemblies 464a, 464b. In this embodiment, the lead lumens 472a, 472b are located on a first transverse side and a second transverse side of the paddle assemblies 464a, 464b, such that the first transverse side is opposite to the second transverse side of the paddle assemblies 464a, 464b. One of skill in the art would understand that the lead anchor 460 may have more than two lead lumens, each lumen capable of being constrained by respective paddles 468 in each of the one or more paddle assemblies 464a, 464b. It will also be understood that the lead lumens and paddles can be arranged in orientations other than on opposite sides of the paddle assemblies.

Also as shown, the lead lumens 472a, 472b and the suture tabs 474 may be located on the same horizontal plane. In other embodiments, the suture tabs 474 may be located at other suitable locations on the lead anchor 460. The suture tabs 474 extend outwards from the body of the outer housing 462.

The actuator 470 is located within a portion of the paddle assembly 464a, 464b and extends longitudinally to the paddles 468 when operated by a user. In the illustrated embodiment, the actuator 470 of the first paddle assembly 464a is accessible from the first end of the lead anchor 460 and the actuator of the second paddle assembly 464b is accessible from the second (opposite) end of the lead anchor 460. This particular arrangement can be useful so that a practitioner can access one of the paddle assemblies 464a, 464b from whichever end of the lead anchor 460 is more accessible. It will be recognized that, at least in some embodiments, it is sufficient to pivot the paddles of only one of the paddle assemblies into the lead lumens to hold the lead or lead extension using the lead anchor. The first and the second ends of the lead anchor 460 are exposed to the user through the outer housing 462 and allow easy access to the respective paddle assembly 464a, 464b adjacent to these ends. A portion of the actuator 470 may slightly extend outside the paddle assembly 464a, 464b from either end of the lead anchor 460 for being accessed.

The paddles 468 can be operably pivoted by the actuator 470 using any suitable mechanism. In at least some embodiments, an operator uses a tool to rotate or push the actuator 470 into the assembly housing 466 and engage it with the paddles 468. For example, the actuator 470 can include a hex fitting or any other suitable fitting (not shown) for receiving a torque wrench or other suitable tool, which rotates or pushes the actuator 470 towards the paddles 468 (see FIG. 5B).

Figure 5A:
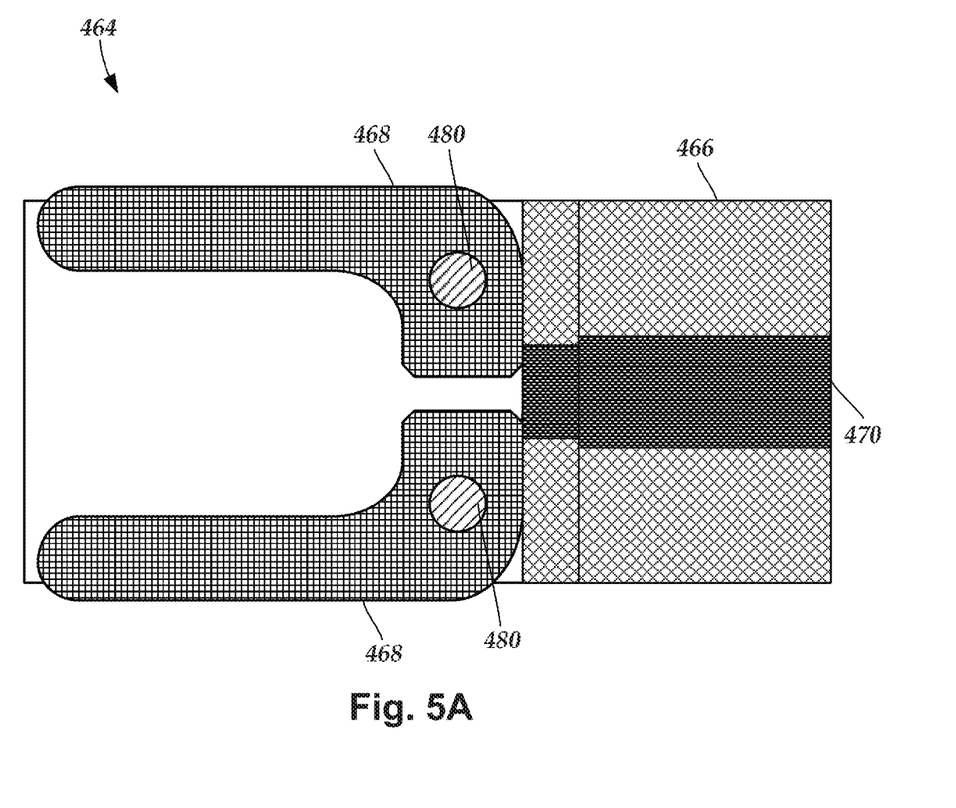
FIG. 5A is a schematic cross-sectional view of a paddle assembly of a lead anchor with the paddles in the closed position, according to the invention.

Turning to FIG. 5A, a schematic cross-sectional view of a paddle assembly 464a, 464b is shown with the paddles 468 in the closed position. In the illustrated embodiment, the paddle assembly 464a, 464b includes two paddles 468 located within the assembly housing 466 and adjacent to the actuator 470 in the closed position. The paddles, in the closed position, may reside completely within the paddle assembly or, in some embodiments, a portion of the paddle may extend out of the paddle assembly so long as it does not prevent insertion of the lead or lead extension into the anchor.

In the illustrated embodiment, each of the paddles 468 is approximately L-shaped having a long arm, a short arm and a curved portion between them. The long arm is positioned substantially along the longitudinal axis of the paddle assembly 464a, 464b and extend adjacent to a lead lumen, for example, (e.g., lumen 472a or lumen 472b in FIG. 4A). The short arm is positioned substantially along the transverse axis of the paddle assembly 464a, 464b, and engages with the actuator 470 in the first portion of the paddle assembly 464a, 464*b*. Each of the paddles 468 is pivotally coupled to the assembly housing 466 via a pivot pin 480, which may be located adjacent to the curved portion of the paddles 468. The pivot pin 480 is inserted into a pivot hole in each of the paddles 468 through the assembly housing 466 to pivotally attach the paddles 468 to the assembly housing 466. In some embodiments, the paddles 468 are of any other shape suitable to pivot out from the assembly housing 466 and extend into the lead lumens 472*a*, 472*b* when the actuator 470 engages with the paddles 468.

Figure 5B:
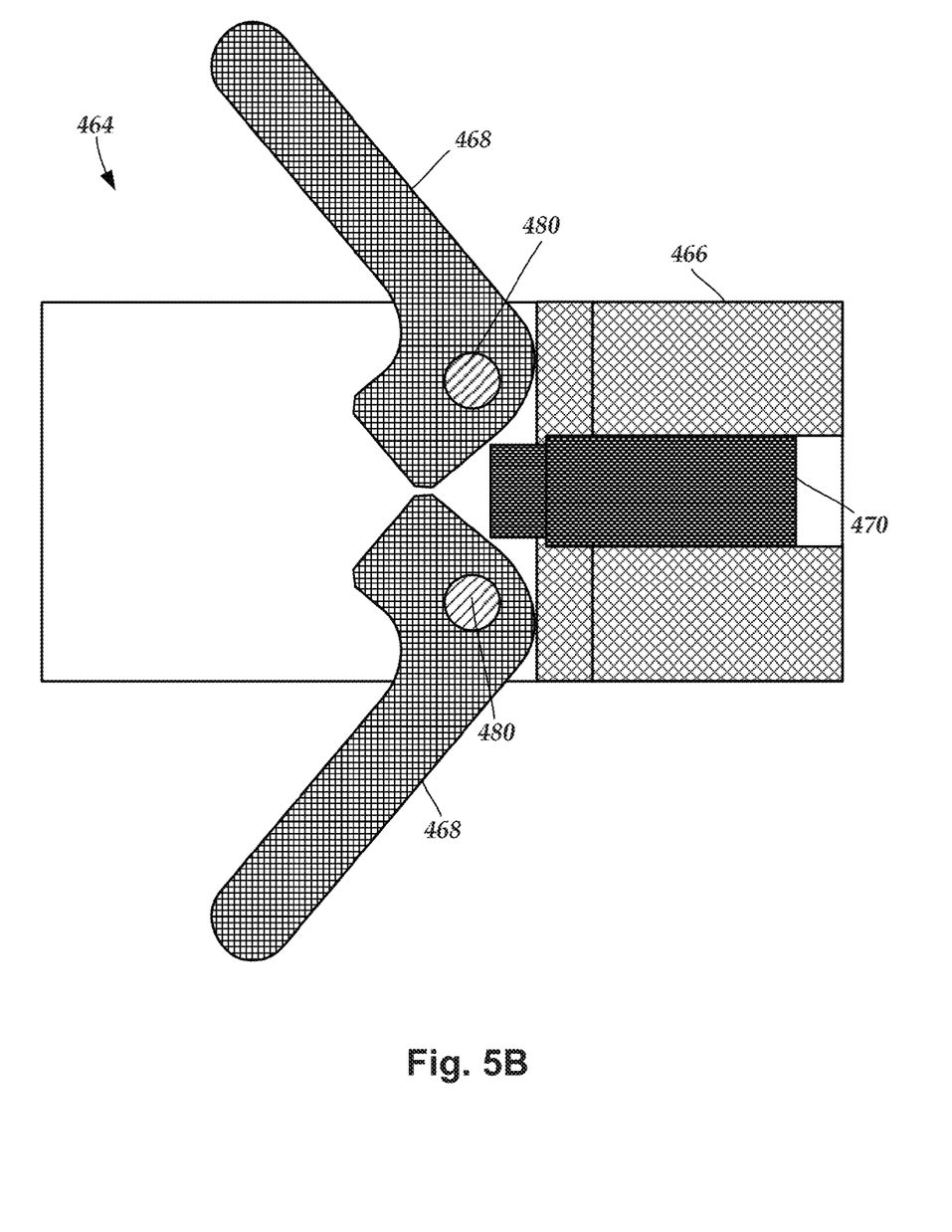
FIG. 5B is a schematic cross-sectional view of a paddle assembly of a lead anchor with the paddles in the open position, according to the invention.

When a user actuates the actuator 470 (such as by rotating a set screw), the paddles 468 are engaged and pivot about the pivot pin 480. The long arms of the paddles 468 move into the lead lumens 472*a*, 472*b* to constrain the leads or lead extensions. The paddles 468 in an open position extending into the lead lumens are illustrated in FIG. 5B.

During operation, a portion of a first electrical stimulation lead is inserted into one of the lead lumens 472*a* adjacent to the paddle assemblies 464*a*, 464*b*. Similarly, a portion of a second electrical stimulation lead may be inserted into another lead lumen 472*b* adjacent to the paddle assemblies 464*a*, 464*b*. The actuator 470 is actuated by a user using the tool for extending the actuator 470 towards the paddles 468 in the paddle assembly 464*a*, 464*b*. The extended actuator 470 pushes the paddles 468 so that the paddles 468 pivot about the pivot pin 480. Consequently, the paddles 468 pivot out from the assembly housing 466. The extended paddles 468 engage, contact, or deflect the leads, such as the lead 103, against the lead lumens 472*a*, 472*b* to create a frictional force between the leads and the lead lumens 472*a*, 472*b*, as well as between the leads and the paddles 468. Such frictional force constrains the movement of the electrical stimulation leads. In some embodiments, the material of the outer housing 462 may be relatively less flexible to assist in increasing the frictional force on the leads, such as the lead 103, for constraining the movement of leads. The lead anchor 460 is then sutured to the patient tissue through the suture holes 476 in the suture tabs 474 via the suture grooves 478 for anchoring the leads.

In at least some embodiments, the actuator 470 can be used to pivot the at least one of the paddles 468 back into the assembly housing 466 and out of contact with the electrical stimulation leads. As a result, the paddles 468 may return to the closed position as shown in FIG. 5A. In at least some embodiments, the paddles 468 remain pivoted into the lead lumens 472*a*, 472*b* irrespective of the actuator 470 being disengaged from the paddles 468. For example, the paddles 468 may engage with a localized locking mechanism within the assembly housing 466 while the paddles 468 are in the open position.

In other embodiments, the paddle assembly 464*a*, 464*b* may include only one paddle for anchoring one lead. Alternatively, the paddle assembly 464*a*, 464*b* may include any number of paddles 468 to constrain more than two leads.

In at least some embodiments, the lead anchor 460 is provided as part of a kit. The kit also includes one or more stimulation leads, such as the lead 103. Alternatively or additionally, the kit may include the control module 102, which may be coupled to the stimulation lead or leads. The specifications or dimensions of the lead anchor 460 can be chosen to match the size and structure of the leads that are to be constrained.

In at least some embodiments, the lead anchor body has tapered ends for deeper insertion within the patient's body. Also, as illustrated in FIGS. 4A-4B, the lead anchor 460 has a rectangular cross-section, however alternative embodiments of the lead anchor may have any other suitable cross-section including, but not limited to, circular, oval, and square. Further, any or all parts of the lead anchor 460 such as the actuator 470 or paddles 468, or a portion of the actuator 470 or paddles, may be made of, or incorporate, a radiopaque material, so that it is visible using fluoroscopy or other forms of X-ray imaging.

Figure 6:
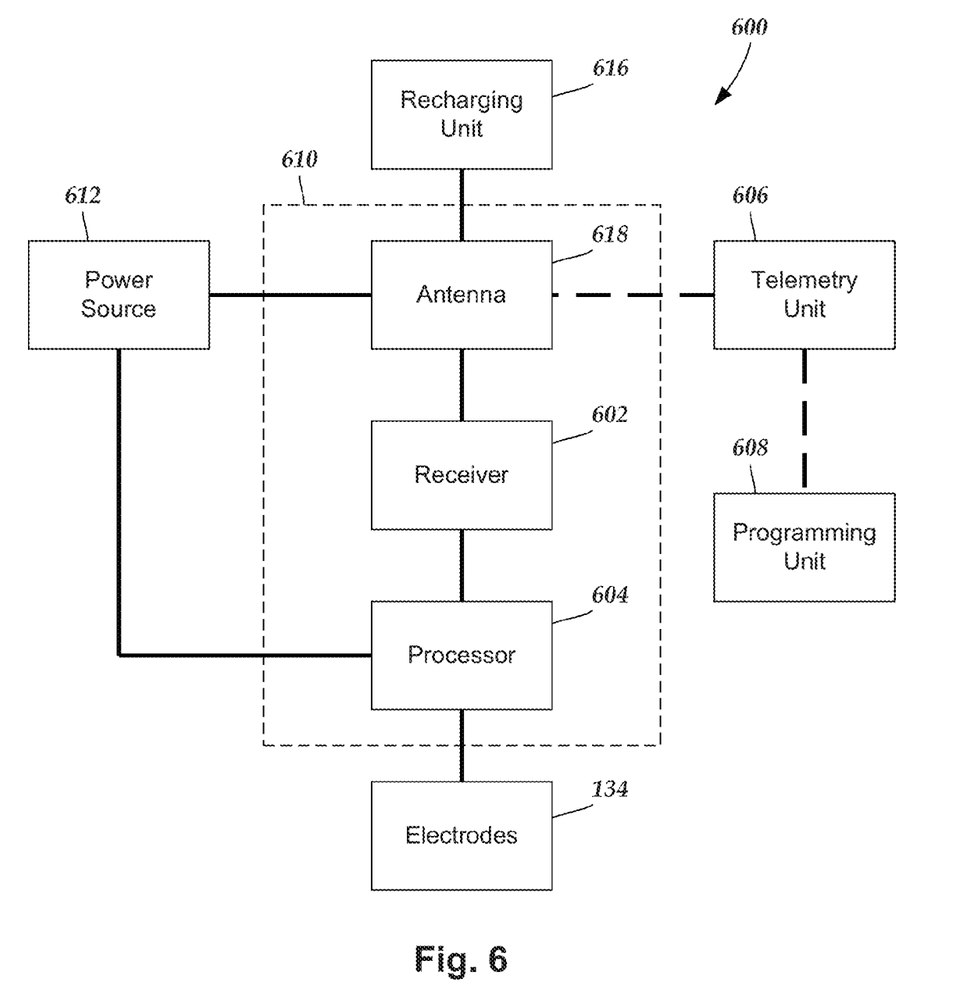
FIG. 6 is a schematic overview of one embodiment of components of a stimulation system, including an electronic subassembly disposed within a control module, according to the invention.

FIG. 6 is a schematic overview of one embodiment of components of an electrical stimulation system 600 including an electronic subassembly 610 disposed within a control module. It will be understood that the electrical stimulation system can include more, fewer, or different components and can have a variety of different configurations including those configurations disclosed in the stimulator references cited herein.

Some of the components (for example, a power source 612, an antenna 618, a receiver 602, and a processor 604) of the electrical stimulation system can be positioned on one or more circuit boards or similar carriers within a sealed housing of an implantable pulse generator, if desired. Any power source 612 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 618 or a secondary antenna. The external power source can be in a device that is mounted on the skin of the user or in a unit that is provided near the user on a permanent or periodic basis.

If the power source 612 is a rechargeable battery, the battery may be recharged using the optional antenna 618, if desired. Power can be provided to the battery for recharging by inductively coupling the battery through the antenna to a recharging unit 616 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 604 is generally included to control the timing and electrical characteristics of the electrical stimulation system. For example, the processor 604 can, if desired, control one or more of the timing, frequency, strength, duration, and waveform of the pulses. In addition, the processor 604 can select which electrodes can be used to provide stimulation, if desired. In some embodiments, the processor 604 selects which electrode(s) are cathodes and which electrode(s) are anodes. In some embodiments, the processor 604 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 608 that, for example, allows modification of pulse characteristics. In the illustrated embodiment, the processor 604 is coupled to a receiver 602 which, in turn, is coupled to the optional antenna 618. This allows the processor 604 to receive instructions from an external source to, for example, direct the pulse characteristics and the selection of electrodes, if desired.

In one embodiment, the antenna 618 is capable of receiving signals (e.g., RF signals) from an external telemetry unit 606 which is programmed by the programming unit 608. The programming unit 608 can be external to, or part of, the telemetry unit 606. The telemetry unit 606 can be a device that is worn on the skin of the user or can be carried by the user and can have a form similar to a pager, cellular phone, or remote control, if desired. As another alternative, the telemetry unit 606 may not be worn or carried by the user but may only be available at a home station or at a clinician's office. The programming unit 608 can be any unit that can provide information to the telemetry unit 606 for transmission to the electrical stimulation system 600. The programming unit 608 can be part of the telemetry unit 606 or can provide signals or information to the telemetry unit 606 via a wireless or wired connection. One example of a suitable programming unit is a computer operated by the user or clinician to send signals to the telemetry unit 606.

The signals sent to the processor 604 via the antenna 618 and the receiver 602 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 600 to cease operation, to start operation, to start charging the battery, or to stop charging the battery. In other embodiments, the stimulation system does not include the antenna 618 or receiver 602 and the processor 604 operates as programmed.

Optionally, the electrical stimulation system 600 may include a transmitter (not shown) coupled to the processor 604 and the antenna 618 for transmitting signals back to the telemetry unit 606 or another unit capable of receiving the signals. For example, the electrical stimulation system 600 may transmit signals indicating whether the electrical stimulation system 600 is operating properly or not or indicating when the battery needs to be charged or the level of charge remaining in the battery. The processor 604 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead anchor, comprising:
    a first paddle assembly comprising an assembly housing, an actuator, and at least one pivotable paddle attached to the housing and operably coupled to the actuator, wherein the at least one pivotable paddle is configured and arranged to pivot out of the assembly housing when a user operates the actuator; and
    a flexible housing disposed around the first paddle assembly and defining at least one lead lumen extending adjacent to the first paddle assembly so that the at least one pivotable paddle pivots into a one of the at least one lead lumen to constrain any lead disposed within the one of the at least one lead lumen.

2. The lead anchor of claim 1, wherein the at least one pivotable paddle is two pivotable paddles and the at least one lead lumen is two lead lumens, wherein each of the two pivotable paddles is configured and arranged to pivot into a respective one of the two lead lumens.

3. The lead anchor of claim 1, wherein the actuator is a screw.

4. The lead anchor of claim 1, wherein the at least one pivotable paddle is retractable using the actuator.

5. The lead anchor of claim 1, further comprising a second paddle assembly disposed within the flexible housing, the second paddle assembly comprising an assembly housing, an actuator, and at least one pivotable paddle attached to the housing and operably coupled to the actuator, wherein the at least one pivotable paddle is configured and arranged to pivot out of the assembly housing when a user operates the actuator, wherein the second paddle assembly is disposed within the flexible housing so that the at least one pivotable paddle of the second paddle assembly pivots into a one of the at least one lead lumen.

6. A kit, comprising:
    a first implantable stimulation lead; and
    the lead anchor of claim 1 configured and arranged to receive a portion of the first implantable stimulation lead within one of the at least one lead lumen of the lead anchor.

7. The kit of claim 6, further comprising a control module coupleable to the first implantable stimulation lead.

8. A method of using a lead anchor, the method comprising:
    inserting a portion of a first electrical stimulation lead into one of the at least one lead lumen of the lead anchor of claim 1; and
    actuating the actuator of the first paddle assembly to pivot the at least one paddle so that at least one of the at least one paddle engages the first electrical stimulation lead and constrains the first electrical stimulation lead within the one of the at least one lead lumen.

9. The method of claim 8, further comprising actuating the actuator to pivot the at least one paddle back into the assembly housing and out of engagement with the first electrical stimulation lead.

10. The method of claim 8, further comprising suturing the lead anchor to patient tissue.

* * * * *